United States Patent [19]
Möhring et al.

[11] 4,127,599
[45] Nov. 28, 1978

[54] PROCESS FOR THE PREPARATION OF POLYISOCYANATES HAVING BIURET GROUPS

[75] Inventors: Edgar Möhring, Bergisch Gladbach; Kuno Wagner; Hanns P. Müller, both of Leverkusen, all of Germany

[73] Assignee: Bayer Aktiengesellschaft, Leverkusen, Germany

[21] Appl. No.: 789,902

[22] Filed: Apr. 22, 1977

[30] Foreign Application Priority Data

May 4, 1976 [DE] Fed. Rep. of Germany ....... 2619548

[51] Int. Cl.² ............................................ C07C 127/24
[52] U.S. Cl. ............................. 260/453 AB; 521/162; 528/144
[58] Field of Search .................................. 260/453 AB

[56] References Cited

U.S. PATENT DOCUMENTS

| 3,862,973 | 1/1975 | Dietrich et al. | 260/453 AB |
| 3,903,126 | 9/1975 | Woerner et al. | 260/453 AB |
| 3,903,127 | 9/1975 | Wagner et al. | 260/453 AB |

Primary Examiner—Dolph H. Torrence
Attorney, Agent, or Firm—Gene Harsh; Lawrence S. Pope

[57] ABSTRACT

The present invention relates to a process for the preparation of polyisocyanates having biuret groups by reaction of excess quantities of organic polyisocyanates with compounds which react with isocyanate groups to form biuret groups, characterized in that the organic polyisocyanates are reacted with a mixture of water and at least one aliphatic, cycloaliphatic or araliphatic monoamine or polyamine.

7 Claims, No Drawings

PROCESS FOR THE PREPARATION OF POLYISOCYANATES HAVING BIURET GROUPS

FIELD OF THE INVENTION

This invention relates to an improved process for the preparation of polyisocyanates having biuret groups by reaction of organic diisocyanates with compounds which react with isocyanate groups to form biuret groups, to the polyisocyanates obtainable by this process and to their use in the production of polyurethane resins by the isocyanate polyaddition process.

BACKGROUND OF THE INVENTION

It is already known, for example, to prepare polyisocyanates having biuret groups from diisocyanates and water as described in German Pat. No. 1,101,394 and U.S. Pat. No. 3,201,372; hydrogen sulphide as described in German Pat. No. 1,165,580 and British Pat. No. 1,043,672; formic acid as described in German Pat. No. 1,174,764 and U.S. Pat. No. 3,392,183 or tertiary alcohols as described in German Pat. No. 1,543,178 and U.S. Pat. No. 3,358,010. In these reactions, amino groups are first formed from part of the isocyanate groups of the diisocyanates put into the process, and these amino groups react with excess diisocyanate to form the polyisocyanates having biuret groups by way of the corresponding urea diisocyanates. These prior art processes have numerous disadvantages. In a heterogeneous reaction of diisocyanates with water, there is a risk of the formation of insoluble polyureas which are difficult to separate out. Furthermore, these prior art processes are always accompanied by the formation of gaseous by-products such as carbon dioxide, carbon monoxide, carbon sulphoxide or olefines. One particularly serious disadvantage of these prior art processes is that part of the isocyanate groups of the diisocyanate used as starting material is invariably destroyed by amine formation. There have, therefore, been no lack of attempts to prepare polyisocyanates having biuret groups by direct reaction of polyamines with polyisocyanates without release of volatile by-products or destruction of isocyanate groups with amine formation. However, all these attempts have met with considerable practical difficulties because of the high reactivity of the amino groups with isocyanate groups, and the formation of insoluble polyureas and cross-linked products is, therefore, very high. The only processes which met with some success were, therefore, those in which very specialized starting materials were used. In German Auslegeschrift No. 1,215,365 and U.S. Pat. No. 3,441,588, for example, it is necessary to use higher molecular weight diaminopolyethers as the diamine component in order to eliminate formation of the above-mentioned difficultly soluble by-products. It goes without saying that the necessity of using diaminopolyethers which must first be prepared by a complicated process cannot provide a commercially completely satisfactory solution to the problem. The process according to German Offenlegungsschrift No. 1,963,190 and U.S. Pat. No. 3,824,266 is restricted to the use of diprimary aromatic diamines which are reduced in their reactivity by steric or electronic effects.

The process according to German Offenlegungsschrift No. 2,261,065 and U.S. Pat. No. 3,903,126 also provides no commercially practicable way of producing polyisocyanates having biuret groups by direct reaction of organic polyisocyanates with simple aliphatic and/or cycloaliphatic polyamines.

Thus, in Example 16 of German Offenlegungsschrift No. 2,261,065 and U.S. Pat. No. 3,903,126 in which polyisocyanates having biuret groups are prepared from hexamethylene diisocyanate and hexamethylene diamine, it is necessary to reheat the reaction mixture to 180° C. for 12 hours to complete the reaction. This long period of reheating at a high temperature is not only uneconomical but causes discoloration of the reaction product, particularly under large scale commercial production conditions, so that the possiblity of using this product in lightfast lacquers is significantly limited.

Although polyisocyanates having a biuret structure, and particularly those based on hexamethylene diisocyanate, have achieved a position of world-wide commercial importance for the production of lightfast and extremely weather-resistant lacquers with maximum gloss retention, these polyisocyanates are manufactured and marketed with as low a proportion of monomeric diisocyanate as possible. Extensive toxicological investigations and many years of experience in the processing of these products have shown that the upper permissible limit of monomer content in these polyisocyanates is about 0.7%, (hexamethylene diisocyanate), based on the solids content, because only then is it possible to ensure that lacquers obtained from these products can be applied without risk to health, and even then only if the usual protective measures for lacquer processing are observed. This upper limit of about 0.7% has been accepted in the literature, e.g. in the leaflet "PUR-Anstrichstoffe" of the Hauptverbandes der deutschen gewerblichen Berufsgenossenschaft and in "Polyurethane Report" of the Paintmakers Association.

Recent extensive investigations have shown that if the aforementioned polymolecular polyisocyanate mixtures having a biuret structure are stored for long periods, particularly under uncontrolled conditions, for example, when transported by ship to hot countries, etc., this limit of about 0.7% of monomeric hexamethylene diisocyanate is exceeded and can easily rise to over about 1% due to catalytic reactions with the walls of the containers if the products are packaged in glass or metal containers. These changes are due to unknown catalytic effects and impurities which cannot be exactly identified analytically, and they also depend on the temperature, which may vary, e.g. between about 20° and 50° C.

Since it is in practice impossible to keep to the monomer limited to about 0.7% in the production of the aforementioned polyisocyanates and the conditions for safe processing of such products has been etablished for more than 10 years, it is of the greatest importance for both commercial and ecological reasons to increase the stability of these products and reduce their rate of decomposition back into monomers and at the same time to reduce the viscosity of the known biuret polyisocyanates based on aliphatic or cycloaliphatic diisocyanates, which is often in the region of about 10,000 to 120,000 cP at 20° C. Such a reduction in the viscosity makes it possible for one and two-component polyurethane lacquers to be produced without solvent. Although a process for the production of exceptionally low viscosity polyisocyanates having a biuret structure, for example biuret polyisocyanates based on hexamethylene diisocyanate, has already been described in U.S. Pat. No. 3,903,127, the polyisocyanates obtainable by this process also have the disadvantage of releasing monomeric hexamethylene diisocyanate during prolonged storage.

It was, therefore, an object of the present invention to provide a process by which polyisocyanates having biuret groups could be prepared substantially without the disadvantages of the processes known in the prior art.

It was surprisingly found that this object could be achieved by using mixtures of water and primary amines as "biuretizing agents". By "biuretizing agents" are meant substances which react with organic isocyanates to form biuret groups.

SUMMARY OF THE INVENTION

The present invention, thus, relates to a process for the preparation of polyisocyanates having biuret groups by reaction of excess quantities of organic polyisocyanates with compounds which react with isocyanate groups to form biuret groups, characterized in that the organic polyisocyanates are reacted with a mixture of water and at least one aliphatic, cycloaliphatic or araliphatic monoamine or polyamine.

DETAILED DESCRIPTION OF THE INVENTION

The process according to the invention provides the following advantages:

1. Since water is not the exclusive biuretizing agent used, the proportion of isocyanate groups which must first be destroyed by amine formation is smaller than in the process according to German Pat. No. 1,101,394 and U.S. Pat. No. 3,201,372 in which water alone is used as biuretizing agent, and the quantity of gaseous by-product (carbon dioxide) released is also reduced;

2. Polyisocyanate mixtures having a biuret structure are obtained which are distinguished by containing an exceptionally high proportion of biuret polyisocyanates of formula I and II indicated below and therefore having an exceptionally low viscosity;

3. The reaction products obtained are light in color and free from gel particles and particularly distinguished from the products of the process according to German Offenlegungsschrift No. 2,261,065 and U.S. Pat. No. 3,903,126 in that they can be freed from excess monomeric diisocyanate without the slightest difficulty, for example, by thin layer distillation;

4. The products of the process are also particularly distinguished by their improved stability in storage, i.e. they have less tendency to split off monomeric starting diisocyanate.

The biuretizing agents used in the process according to the invention, that is to say substances which react with isocyanates to form biuret groups, are mixtures of amines and water.

In the biuretizing agents used according to the invention, the proportion of amine components to water may vary within a very wide range which moreover is not critical. The equivalent ratio of primary amino groups to water in the biuretizing agents used according to the invention is generally between about 5:1 and 1:5. When monoamines are used, the equivalent ratio is preferably between about 2:1 and 1:2.

When diamines are used, as is preferred for this process, the equivalent ratio is preferably from about 3:1 to 1:1 and most preferably about 2:1. An equivalent ratio of about 1:1 means in this context that one molecule of water is present to one primary amino group of the amine.

The fact that mixtures of amines and water are quite different in their reactivity with isocyanate groups than the pure amines or water alone is extremely surprising. In fact, one would have expected that the high reactivity of amines with isocyanate groups, which is the main cause for the difficulties hitherto encountered in the preparation of biuret polyisocyanates by the reaction of diisocyanates with free amines, would not be reduced by the presence of water. On the other hand, one would have expected that water, which is, of course, much less reactive than amines, would be much slower to react with isocyanates than an amine present in the mixture. However, the biuretizing agents according to the invention behave as uniform compounds in their reaction with isocyanate groups, that is to say they react much more slowly with isocyanates than the corresponding amines but much more rapidly than water.

The process according to the invention is carried out by reacting the biuretizing agents according to the invention with an excess of polyisocyanate. There is, in principle, no limit to the amount of polyisocyanate excess which may be used, but the proportions of reactants are generally chosen so that the molar ratio of (primary amino groups + water) : isocyanate groups is from about 1:3 to 1:100, preferably from about 1:4 to 1:12. The reaction is generally carried out at a temperature of from about 60° to 200° C, preferably from about 120° to 180° C. If cloudiness appears in the reaction mixture, it can be eliminated by brief heating to about 160° to 180° C. The temperature of the reaction mixture is generally kept at about 130° to 160° C. for a further about 1 to 6 hours after all the reactants have been introduced. The excess of monomeric diisocyanate or polyisocyanate may subsequently be removed, e.g. by thin layer evaporation. According to one particular method of carrying out the process, the mixture of amine and water is vaporized at a temperature of from about 140° to 180° C and introduced in this form into the polyisocyanate, if desired together with an inert gas (e.g. nitrogen). This method ensures extremely fine distribution of the mixture of amine and water in the polyisocyanate.

The amines used for the process according to the invention are organic amines having 1 or 2 aliphatically or cycloaliphatically bound primary amino groups. Amines of this kind include, for example, aliphatic, cycloaliphatic or araliphatic monoamines of the formula R—$NH_2$ where R represents an aliphatic hydrocarbon group having 1 to 12 carbon atoms, a cycloaliphatic hydrocarbon group having 5 to 7 carbon atoms or an araliphatic hydrocarbon group having 7 to 8 carbon atoms e.g. methylamine, n-butylamine, n-dodecylamine, cyclopentylamine, cyclohexylamine, cycloheptylamine, benzylamine or 2-phenyl-ethylamine. The amines preferably used in the process according to the invention are polyamines having two aliphatically or cycloaliphatically bound primary amino groups. Examples of such amines include diprimary diamines of the formula R' $(NH_2)_2$ in which R' represents an aliphatic hydrocarbon group having 2 to 12 carbon atoms; a cycloaliphatic hydrocarbon group having 4 to 17 carbon atoms or an araliphatic hydrocarbon group having 8 to 10 carbon atoms, e.g. ethylene diamine; propylene-1,2- and -1,3-diamine; 1,4-diaminobutane; 2,2-dimethyl-propane-1,3-diamine; 1,6-diaminohexane; 2,5-dimethylhexane-2,5-diamine, 2,2,4-trimethylhexane-1,6-diamine; 1,8-diaminooctane; 1,10-diaminodecane; 1,11-diaminoundecane; 1,12-diaminododecane; 1-methyl-4-

(aminoisopropyl)-1-cyclohexylamine; 3-aminomethyl-3,5,5-trimethyl-1-cyclohexylamine; 1,2-bis-(aminomethyl)-cyclobutane; p-xylylene diamine; 1,4-bis-(2-aminoethyl)-benzene; 1,2- and 1,4-diaminocyclohexane; 1,2-, 1,4-, 1,5- and 1,8-diaminodecaline; 1-methyl-4-aminoisopropyl-1-cyclohexylamine; 4,4'-diamino-dicyclohexylmethane; 2,2'-bis-(4-amino-cyclohexyl)-propane; 3,3'-dimethyl-4,4'-diamino-dicyclohexylmethane; 1,2-bis-(4-aminocyclohexyl)-ethane and 3,3', 5,5'-tetramethyl-bis-(4-aminocyclohexyl)-methane and -propane-(2,2).

Other polyamines also suitable for the process according to the invention include bis-(aminoalkyl)-amines preferably having a total of from 4 to 12 carbon atoms, e.g. bis-(2-aminoethyl)-amine; bis-(3-aminopropyl)-amine; bis-(4-aminobutyl)-amine and bis-(6-aminohexyl)-amine as well as isomeric mixtures of dipropylenetriamine and dibutylene triamine. Such polyamines containing secondary amino groups are, however, less preferred.

It is particularly preferred to use tetramethylene diamine or 1,2-bis-(aminomethyl)-cyclobutane or, especially, hexamethylenediamine.

Suitable polyisocyanates for the process according to the invention include in particular diisocyanates of the formula Q(NCO)$_2$ in which Q represents an aromatic hydrocarbon group having from 6 to 15 carbon atoms, an araliphatic hydrocarbon group having from 8 to 10 carbon atoms, in particular one having 8 carbon atoms; an aliphatic hydrocarbon group having from 4 to 12 carbon atoms or a cycloaliphatic hydrocarbon group having from 4 to 15 carbon atoms. Examples of such isocyanates include tolylene-2,4- and -2,6-diisocyanate and isomeric mixtures thereof; diphenylmethane-4,4'- and -2,4'-diisocyanate, xylylene diisocyanate or 1,4-bis-(2-isocyanatoethyl)-benzene. Particularly suitable are aliphatic and cycloaliphatic diisocyanates such as 1,4-diisocyanatobutane; 1,6-diisocyanatohexane; 2,4,4-trimethylhexane-1,6-diisocyanate; 1,11-diisocyanatoundecane; 3-isocyanatomethyl-3,5,5-trimethylcyclohexyl isocyanate-(1); cyclohexane-4,4'-diisocyanate; dicyclohexylmethane-4,4'-diisocyanate or 1,2-bis-(isocyanatomethyl)-cyclobutane. Hexamethylene diisocyanate is particularly preferred.

The products obtained from the process according to the invention are particularly light in color if the diisocyanate used as starting material is pretreated by heating it for about 6 to 10 hours at from about 120° to 195° C., preferably about 160° to 180° C and then distilled.

The biuret polyisocyanates obtained by the process according to the invention are generally clear and colorless to light yellowish with a viscosity at 25° C of from about 1000 to about 100,000 preferably of from about 1000 to about 20,000 cP. If the preferred diamines are used in the process, then the products, regardless of the diisocyanate excess used, consist predominantly of compounds of formula I

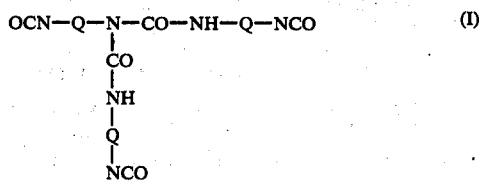

and formula II

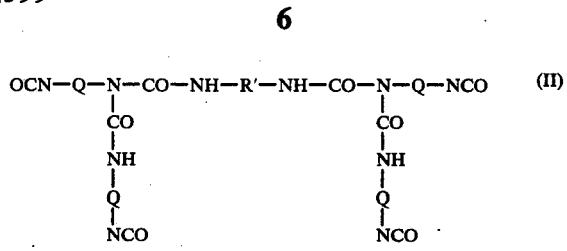

in which Q and R' have the meaning already specified.

When starting materials of corresponding constitution are reacted together, e.g. hexamethylene diamine/water with hexamethylene diisocyanate (Q = R' = (CH$_2$)$_6$), transbiuretization reactions take place and the process according to the invention yields biuret polyisocyanate mixtures containing an exceptionally high proportion of monobiurets of formula (I), and this result again is produced largely independently of the selected diisocyanate excess.

This means that exceptionally low viscosity biuret polyisocyanate mixtures containing an exceptionally high proportion of monobiurets can be obtained very simply by the process according to the invention if diisocyanates and diamines of corresponding constitution (Q=R') are used.

The products according to the invention are surprisingly readily soluble in the usual lacquer solvents such as acetone, dioxane, tetrahydrofuran, benzene, xylene, ethyl acetate or ethyl glycol acetate.

The products of the process may be used e.g. as crude solutions in the excess diisocyanates from which they were prepared or in isolated form or in any mixtures with other polyisocyanates, for the production or modification of synthetic resins, foams of all kinds and lacquer coatings.

It is particularly advantageous to use the products, after they have been prepared and freed from monomeric diisocyanates and polyisocyanates, as physiologically harmless polyisocyanates for the production of lacquer coatings. For this purpose, they may be used alone or they may be used in combination with polyisocyanates conventionally used for lacquer coatings in order to modify the properties of the lacquer coatings. Reaction products which are free from monomer are also particularly suitable for the production of single component lacquers because they react with the atmospheric moisture in the presence of suitable catalysts rapidly from dust-dry surfaces and become cross-linked and insoluble within a short time.

The products of the process may also be used for the production of lightfast foams and porous synthetic resins which have a high density and smooth surface skin.

The products may also be grafted in the presence of radical forming agents such as acrylic acid derivatives or other suitable compounds to give rise to modified polyisocyanates which have valuable properties.

The economical method of production and optimum compatibility of the products of the process with acrylates, polyethers and polyesters should be particularly pointed out. Another advantage compared with all previously known processes in the present state of the art is the possibility of obtaining products with a very low viscosity even when only a very slight polyisocyanate excess is used.

The parts given in the following Examples are parts by weight.

EXAMPLES

EXAMPLE 1

5.4 Parts (0.3 mol) of water were added to 34.8 parts (0.3 mol) of hexamethylenediamine and the mixture was homogenized. It was then introduced dropwise into 1009 parts (6.0 mol) of hexamethylenediisocyanate at 170° C. The reaction mixture was then stirred for 2 hours at 170° C and 1 hour at 150° C. Any particles floating in the reaction mixture were removed. The clear reaction solution was then freed from excess hexamethylene diisocyanate by thin layer evaporation at 160° C/0.5 Torr. 272 Parts of a clear, colorless polyisocyanate having biuret groups was obtained. It had an isocyanate content of 21.8% by weight and a viscosity of 4033 cP/25° C.

The product had the following composition according to gel chromatographic analysis:

0.1% of 1,6-diisocyanatohexane,
44.5% of monobiuret,
17.4% of bis-biuret,
9.5% of tris-biuret,
5.4% of tetra-biuret and
23.1% of unidentified or higher molecular weight constituents.

The stability of the polyisocyanate mixture in storage, i.e., its resistance to decomposition with the formation of hexamethylene diisocyanate (HDI), was tested by storing four samples of the mixture at 25° C and 50° C for 2 weeks and 4 weeks, respectively, and then determining the free hexamethylene diisocyanate content by gas chromatograhic analysis. The results obtained are summarized in the following Table.

TABLE

| Length of storage time | Storage temperature | HDI content |
|---|---|---|
| 14 days | 25° C | 0.25% |
| 28 days | 25° C | 0.32% |
| 14 days | 50° C | 0.38% |
| 28 days | 50° C | 0.47% |

EXAMPLE 2

35.2 Parts (0.4 mol) of tetramethylenediamine and 7.2 parts (0.4 mol) of water were mixed and then introduced dropwise into 1211 parts (7.2 mol) of hexamethylene diisocyanate at 100° C. Stirring was continued for a further 5 hours at 180° C. The product was treated as described in Example 1. 329 Parts of a clear, golden yellow polyisocyanate which contained biuret groups and had an isocyanate content of 20.0% by weight and a viscosity at 25° C of 18,312 cP were obtained.

EXAMPLE 3

22.2 Parts (0.3 mol) of propylene-1,2-diamine were mixed with 5.4 parts (0.3 mol) of water and introduced dropwise into 1211 parts (7.2 mol) of hexamethylene diisocyanate at 190° C. Stirring was then continued for 1 hour at the same temperature. The product was processed as described in Example 1. 233 Parts of a clear, slightly yellowish polyisocyanate which contained biuret groups and had an isocyanate content of 19.6% by weight and a viscosity at 25° C of 12,862 cP were obtained.

EXAMPLE 4

18 Parts (0.3 mol) of ethylenediamine were mixed with 5.4 parts (0.3 mol) of water, very vigorous evolution of heat taking place. The mixture was introduced dropwise into 1211 parts (7.2 mol) of hexamethylene diisocyanate at 100° C. The reaction mixture was then stirred for 5 hours at 180° C. The product was treated as described in Example 1. 182 parts of a clear, colorless polyisocyanate which contained biuret groups and had an isocvanate content of 20.2% by weight and a viscosity at 25° C of 5585 cP were obtained.

EXAMPLE 5

61.9 Parts (0.6 mol) of diethylene triamine were mixed with 8.1 parts (0.45 mol) of water and then introduced into 1211 parts (7.2 mol) of hexamethylene diisocyanate at 160° C. The mixture was then stirred for 1 hour at 180° C. The product was processed as described in Example 1. 243 Parts of a clear, light yellow polyisocyanate which contained biuret groups and had an isocyanate content of 13.6% by weight and a viscosity at 25° C of > 90,000 cP were obtained.

EXAMPLE 6

102.2 Parts (0.6 mol) of isophorone diamine were mixed with 5.4 parts (0.3 mol) of water. The mixture was introduced dropwise into 1211 parts (7.2 mol) of hexamethylene diisocyanate at 160° C. It was then stirred for 1 hour at the same temperature. The product was treated as described in Example 1. 492 Parts of a colorless, clear polyisocyanate which contained biuret groups and had an isocyanate content of 19.4% by and a viscosity at 25° C of about 81,750 cP were obtained.

EXAMPLE 7

This example describes the preparation of a colorless biuret polyisocyanate which contains biuret groups, from hexamethylene diisocyanate and hexamethylene diamine/water by a method similar to that of Example 1. In contrast to the method of Example 1, the hexamethylene used in this case was subjected before the process to 8 hours of heat treatment at 180° C to destroy unknown impurities and catalytically active compounds and was then purified by distillation. The procedure was otherwise exactly as described in Example 1. 316 Parts of water-clear biuret polyisocyanate mixture having an isocyanate content of 22.2% by weight and a viscosity at 25° C of 5559 cP was obtained.

Gel chromatographic analysis indicated the following composition:

0.5% of 1,6-diisocyanatohexane.
44.6% of monobiuret,
17.8% of bis-biuret,
9.9% of tris-biuret,
5.2% of tetra-biuret
21.9% of unidentified or higher molecular weight constituents.

EXAMPLE 8 (Comparison Example)

The following comparison example was carried out in three variations (a), (b) and (c) to demonstrate that the preparation of polyisocyanates having biuret groups by the procedure described in Example 16 of German Offenlegungsschrift No. 2,261,065 and U.S. Pat. No. 3,903,126 is hardly a practical commercial process since it is also accompanied by the disadvantageous phenomena described in German Patent No. 1,770,927 which corresponds to Canadian Pat. No. 876,735. The erratic reaction mentioned in German Pat. No. 1,770,927, which gives rise to non-homogeneous reaction products and is attributed to the high reactivity of the amine component, is also observed when the process according to Example 16 of German Offenlegungsschrift No. 2,261,065 and U.S. Pat. No. 3,903,126 is employed. In particular, a repetition of the method described in Example 16 of German Offenlegungsschrift No. 2,261,065 and U.S. Pat. No. 3,903,126 confirms the conclusion drawn in German Pat. No. 1,770,927 that, when large reaction batches are used, considerable difficulties arise from the fact that large quantities of insoluble polyureas and cross-linked products are formed. Although these products can be broken down again at temperatures of about 200° C, such a procedure favors the formation of unwanted, strongly colored by-products due to the excessive heating of the reaction mixture.

VARIATION (a)

(corresponding Example 16 of German Offenlegungsschrift No. 2,261,065 and U.S. Pat. No. 3,903,126)

14.5 Parts (0.125 mol) of hexamethylene diamine which has been heated to 70° C are added to 168 parts (1 mol) of hexamethylene-1,6-diisocyanate with stirring over a period of 20 minutes at about 25° C in a nitrogen atmosphere.

Spontaneous precipitation of completely insoluble higher molecular weight $\alpha,\omega$-diisocyanatopolyurea substances having a pasty consistency sets in at once. The polyureas cannot be observed to dissolve evenly. Biuretization proceeds extremely slowly and must be assisted by stirring the reaction mixture at 180° C. for 12 hours, during which time the solution turns yellow with a reddish tinge. The mixture (yield about 182 parts by weight) contains pulverulent constituents and gel particles and about 20% by weight of monomeric hexamethylene diisocyanate. It contains a total of 3.5 parts by weight of decomposed, unreacted polybiuret polyureas which can be broken down only very slowly at 200° C. by reactions involving splitting and transbiuretization. When attempts are made to filter this solution, the filter is immediately plugged by glass-clear gel particles. After isolation of the solution by centrifuging followed by removal of the monomer by thin layer distillation, a polyisocyanate mixture with biuret groups is obtained which is yellowish brown with a reddish tinge. The product has an isocyanate content of 17.1% and a viscosity about 143,000 cP/25° C. It is completely unsuitable for the production of light-fast, high gloss lacquer films intended to be cross-linked by moisture. 25 Parts by weight of the product are cross-linked during thin layer distillation, thereby seriously interfering with the process of removing the monomer.

VARIATION (b)

The procedure is exactly the same as in (a) but using 10 times the quantities. The time required for introduction of the hexamethylenediamine is 20 minutes. The pasty polyureas cannot be observed to dissolve evenly. The procedure is otherwise the same as under (a). The reddish, yellow-brown end product is impossible to filter since it contains a much higher proportion of pulverulent constituents and gel particles (about 45 parts by weight) than in experiment (a). To obtain a gel-free mixture, it is necessary to centrifuge the reaction mixture and then decant it to remove the gel constituents. After removal of the monomer by thin layer distillation, the reaction product is deep brown in color.

The thin layer evaporator breaks down after 2 hours of continuous operation due to the formation of cross-linked components.

VARIATION (c)

The procedure is the same as in (b) except that the rate of addition of hexamethylenediamine is slowed down by a factor of 10, which means that hexamethylenediamine is introduced dropwise over a period of 200 minutes. The procedure is otherwise the same as in (a) and (b). This variation (c) again requires extremely long reaction times of at least 12 hours. The same filtration difficulties occur as in experiment (b). After purification by a tedious thin layer distillation process, the end product is completely unsuitable for the production of light-fast, high gloss two-component lacquers by reaction with hydroxyl esters.

$\eta 75°$ C 29,100 cP.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of polyisocyanates having biuret groups comprising reacting excess quantities of organic polyisocyanates of the formula $Q(NCO)_2$ wherein Q represents a aliphatic hydrocarbon group having from 4 to 12 carbon atoms or a cycloaliphatic hydrocarbon group having from 4 to 15 carbon atoms with a mixture of water and diprimary diamines of the formula $R'(NH_2)_2$ wherein $R'$ represents an aliphatic hydrocarbon group having 2 to 12 carbon atoms, a cycloaliphatic hydrocarbon group having 4 to 17 carbon atoms, or an araliphatic hydrocarbon group having 8 to 10 carbon atoms.

2. Process according to claim 1, characterized in that the organic polyisocyanates are reacted with quantities of the mixture of water and amine such that the molar ratio of (NCO groups of the diisocyanate): ($H_2O$ + primary amino groups of the amine) present in the reaction mixture is between about 3 : 1 and 100 : 1.

3. Process according to claim 1, characterized in that the water and amine are used in quantities corresponding to an equivalent ratio of water : primary amino groups of between about 5 : 1 and 1 : 5.

4. Process according to claim 1, characterized in that the polyisocyanates to be used in the process are pretreated before use by heating for about 6 to 10 hours at about 120° to 195° C and are then distilled.

5. Process according to claim 1, characterized in that the mixture of water and amine is reacted in vapor form with the polyisocyanates which have been heated to a temperature of from about 60° to 200° C.

6. Polyisocyanates having biuret groups produced by the process of claim 1.

7. The process of claim 1, wherein the diprimary diamines are selected from the group consisting of tetramethylene diamine, 1,2-bis-(aminomethyl)-cyclobutane and hexamethylenediamine and the organic polyisocyanate is hexamethylene diisocyanate.

* * * * *